(12) United States Patent  
Wardlaw (10) Patent No.: US 8,506,630 B2  
(45) Date of Patent: Aug. 13, 2013

(54) INTERVERTEBRAL DISC PROSTHESIS

(75) Inventor: Douglas Wardlaw, Aberdeen (GB)

(73) Assignee: Grampian Health Board, Aberdeen (GB)

( * ) Notice: Subject to any disclaimer, the term of this patent is extended or adjusted under 35 U.S.C. 154(b) by 0 days.

(21) Appl. No.: 12/721,095

(22) Filed: Mar. 10, 2010

(65) Prior Publication Data

US 2010/0168859 A1    Jul. 1, 2010

Related U.S. Application Data

(63) Continuation of application No. 10/496,215, filed as application No. PCT/GB02/05210 on Nov. 19, 2002, now abandoned.

(30) Foreign Application Priority Data

Nov. 19, 2001   (GB) .................................. 0127697.1

(51) Int. Cl.  
     *A61F 2/44*      (2006.01)

(52) U.S. Cl.  
     USPC ........................................ 623/17.11

(58) Field of Classification Search  
     USPC ................ 623/17.11, 17.12, 17.16; 606/246  
     See application file for complete search history.

(56) References Cited

U.S. PATENT DOCUMENTS

| | | | |
|---|---|---|---|
| 4,772,287 A * | 9/1988 | Ray et al. | ................... 623/17.12 |
| 5,571,189 A | 11/1996 | Kuslich | |
| 5,645,597 A | 7/1997 | Krapiva | |
| 5,997,582 A | 12/1999 | Weiss | |
| 2004/0186576 A1* | 9/2004 | Biscup et al. | ............... 623/17.12 |

FOREIGN PATENT DOCUMENTS

WO      WO 99/02108      1/1999

* cited by examiner

*Primary Examiner* — Eduardo C Robert  
*Assistant Examiner* — David Comstock  
(74) *Attorney, Agent, or Firm* — Licata & Tyrrell P.C.

(57) ABSTRACT

A flexible prosthetic cover shaped to form a replacement nucleus pulposis for an intervetebral disc with an aperture for the introduction of filling material therein, and an elongate introducer member configured to pass into the aperture is provided. The cover has a strengthened portion substantially opposite the aperture for engaging the distal end of the member, the strengthened portion and the distal end being arranged to interlock, for facilitating orientation of the cover, for example so as to prevent relative rotation there between.

30 Claims, 8 Drawing Sheets

INTERVERTEBRAL DISC PROSTHESIS

This patent application is a continuation of U.S. patent application Ser. No. 10/496,215 filed on Nov. 8, 2004 now abandoned which is the U.S. National Phase of PCT/GB02/05210, filed Nov. 19, 2002 which claims the benefit of priority from GB 0127697.1, filed Nov. 19, 2001, teachings of each of which are herein incorporated by reference in their entirety.

FIELD OF THE INVENTION

The present invention relates to an intervertebral disc insert for containing filling material, hydrogel or a biological replacement of a nucleus pulposis, in the form of a prosthetic jacket or cover. Such a prosthesis may be used to perform interbody fusion or to replace damaged nucleus pulposis with hydrogel or cells and matrix as a biological replacement. Such devices are useful to replace damaged disc nuclei, whether in the lumbar or other region of the spine, for example using a percutaneous fusion technique.

BACKGROUND OF THE INVENTION

The normal intervertebral disc is a highly specialized joint between the intervertebral bodies from the second cervical vertebra to the first sacral vertebra in the human body. A disc is made up of a strong outer ring called the annulus, which is strongly attached to the intervertebral bodies above and below through collagen fibers, and a central nucleus. The nucleus comprises a mesh of collagen fibers to which is attached proteoglycan molecules which are hygroscopic. It can therefore be said to consist of a central portion and an intermediate zone. The central portion comprises 90% proteoglycan and 10% collagen, and the intermediate zone rather less proteoglycan and proportionately more collagen. The annulus comprises 90% collagen with about 10% proteoglycan, which proteoglycan acts to allow a sliding motion between adjacent layers during normal daily use.

Like all other joints in the body, intervertebral discs, particularly lumbar intervertebral discs, are subject to various types of injury, degeneration and disease. Painful disc syndromes can develop due to the destruction of the intervertebral disc structure.

It is often the case that back pain emanating from an intervertebral disc arises from a damaged annulus because the outermost third of the annulus itself is the only part of the disc structure which is innervated. In theory then, the insertion of a prosthesis which has itself a finite structure with inherent strength but at the same time is held in position by the annulus would permit the annulus itself to heal with the commensurate relief of pain.

Such a prosthesis has been suggested by the present applicant in WO 99/02108. This provides an intervertebral disc nucleus prosthesis generally comprising a transudative or ion transport material extended over the inner face of a prosthetic woven or porous fabric chosen for its strength and immunological neutrality. With this design, tissue can grow over and incorporate the outer fabric, while water and very low molecular weight materials can pass through the prosthetic fabric and the transudative membrane, thus eliminating, or at least substantially alleviating, any immunological problems. This allows the anchoring of the replacement nucleus pulposis within a disc space while preventing the ingrowth of bony trabeculae, thereby providing a more satisfactory long term solution.

An alternative arrangement generally comprises a three layer cover, wherein the outer and inner layer are formed of a strong material in a sandwich construction with a middle layer of a transudative material of a small pore size. Very high pressures are present in use within the normal disc nucleus. To counteract this it is often necessary to introduce a hydrogel or other suitable substance into the cover in a liquid or powdered state. Thus, the hydrogel would have a tendency to escape through the cover were it not so constructed as to combine strength with an ability to retain the hydrogel which might otherwise leak out through the pores in the cover. This alternative jacket construction addresses this concern. Furthermore, materials have been developed which have both strength and also function as a transducive membrane, e.g. Goretex.

Another alternative arrangement is to have a cover of a relatively impermeable material, for example polyurethane, which is both strong and bio-compatible. In such arrangements, a hydrogel and water mixture can be added in a predefined amount and ratio, so as to produce a consistency which substantially replicates the properties of the natural nucleus.

The various prosthetic arrangements described above remain in position due to the snug fit within the annulus, and by virtue of the prosthesis being considerably larger than the hole in the annulus through which it was originally inserted. Also, adhesions will develop between the prosthesis and the annulus over time.

Orientation of the prosthesis is facilitated by introducing apparatus including a tubular external valve body which may be internally screw threaded. An introducer rod is passed through the body and may have an external screw thread for engagement therewith. The rod thus serves as a stiffening device for positioning the cover in the disc cavity. Where screw threads are provided, rotation of the rod extends or retracts the distal end of the rod further to facilitate orientation of the cover. The cover preferably has a strengthened portion opposite the valve in which the distal end of the rod may be seated.

BRIEF DESCRIPTION OF THE DRAWINGS

FIG. 3 shows in FIG. 3A a vertical section through an intervertebral disc in the process of removal of a damaged nucleus pulposis;

FIG. 4, shows in FIG. 4A a cross-section a prosthetic cover in accordance with the present invention being introduced between adjacent vertebrae, whereas

FIG. 5 shows in FIG. 5A the insertion of a hydrogel into the prosthesis in accordance with the present invention in vertical cross-section, whereas

FIG. 6 shows in FIG. 6A a vertical cross-section of the completed prosthesis, while FIG. 7 shows in FIGS. 7A and 7B alternative embodiments of a further prosthesis and introducer rod according to the invention.

DETAILED DESCRIPTION OF THE INVENTION

According to the present invention, there is provided a flexible prosthetic cover shaped to form a replacement nucleus pulposis for an intervertebral disc and comprising an aperture for the introduction of filling material therein, and an elongate introducer member configured to pass into the aperture, the cover having a strengthened portion substantially opposite the aperture for engaging the distal end of the member, the strengthened portion and the said distal end being arranged to interlock so as to prevent relative rotation there between, for facilitating orientation of the cover. The aperture preferably comprises an internal valve such as a flap valve. Thus the cover may be accurately seated within the disc space without the need for an external valve body.

In one embodiment, the distal end of the introducer member or rod may be cruciate or flat, and the strengthened portion may be a seat having a correspondingly shaped slot or cross-shaped recess for receiving it. Thus, the surgeon may extend the prosthesis into the cavity between the adjacent vertebrae, using the introducer rod as a temporary stiffening device. With the introducer rod seated in the edge portion of the prosthesis, the cover is held in the required orientation, and precise alignment may be achieved by rotating the introducer rod.

Preferably, the strengthened portion comprises a radio-opaque marker for indicating the position or orientation of the strengthened portion, and thus of the cover.

The introducer member may have an internal channel and an aperture at or adjacent the distal end therefore communicating with the channel for allowing the injection of filling material into the cover. Thus no further equipment will be required for injecting the filling material. Alternatively, the aperture may be arranged to accept an introducer tube shaped to pass over the introducer member and to form a channel there between for allowing the injection of filling material into the cover, after removal of the introducer member.

The introducer member may comprise a balloon, such that when the cover is inserted into a nuclear cavity in a rolled or folded state, the balloon may be inflated to cause the cover to unfold and fill the nuclear cavity. Such an arrangement may be important where the cover is designed for a percutaneous fusion procedure, for example as outlined below.

The cover may include a deformable porous body shaped to fit within the cover, formed for example of a very fine mesh or very loose roll or sponge of material. This may for example be made up of very fine polypropylene or other material. The body is formed in such a way that it may be inserted into the cover through the aperture either before the cover is inserted into the disc nucleus cavity, or when the cover is in place. The body may be attached to the cover. Thus, once the filling material such as hydrogel is introduced its properties may effectively be altered such that it will not flow as a liquid, but will deform in a way more similar to the natural disc nucleus.

Where the disc nucleus has degenerated to an extent beyond that in which a prosthetic disc nucleus (as discussed above) can usefully be inserted, then an alternative is to carry out a percutaneous fusion on the affected intervertebral segment.

According to the present invention there is also provided a prosthetic cover for an intervertebral disc comprising an edge portion comprising a resiliently deformable annular sleeve, and a pair of opposed central portions each joining an edge of the sleeve, the edge portion including an aperture for the introduction of a filling material.

Preferably, the central portions are arranged, when the cover is filled with a filling material, to allow the filling material to pass there through.

For example, the central portions may be formed of a weaker material than that of the edge portion, which under pressure will give to allow the filling material to burst through pores or weakened layers in it. Advantageously the material of the central portion may be made of a material which is not only weakened but will reabsorb in time allowing replacement by bone or other material so introduced. Alternatively, it may be made of an open weave or such structure as will allow the filling material to easily pass there through and come into contact with the bone of the end plates. It may allow blood vessels from the adjacent end plate bone to pass through it, and grow into the bone graft or other material placed inside the cover, to allow vascularisation of bone graft and conversion to solid bone.

Thus, the prosthetic cover may be inserted, in the form of a substantially kidney shaped balloon, into the disc cavity following removal of the nucleus in such a way that it fits the shape of the cavity. The annular sleeve, generally in the shape of a car tyre, fits within the disc annulus, with the thin central portions adjacent the end plates of the superior and inferior vertebral bodies. When a filling material is injected into the cover under pressure, the material breaks the weakened central portions, or bursts through the open weave, and pressurizes the annular sleeve against the annulus, thereby preventing its escape through any weaknesses or tears in the disc annulus that may be present.

The end plates of the vertebral bodies are preferably prepared by creating holes in them. When the filling material, which may be cement or bone substitute material, bursts through the central portions, it may communicate directly with the prepared end plates of the vertebral bodies, and "key" into holes created in them.

Seating of the cover may alternatively be achieved by insertion of a balloon catheter into the cover, which is inflated to fill the inside thereof. After ensuring correct seating, the balloon is deflated and an outer filling tube is passed over it into the cover. The balloon may then be removed and the material injected.

The aperture may be provided as part of a valve structure, which is preferably formed of an imaging transparent material, for example titanium, carbon fibre or a durable biocompatible plastics material such as polypropylene. In one preferred embodiment, the valve structure includes a one way valve arrangement which may be a flap valve partially attached to an inside of the cover, such that the valve structure will be in a closed state when an internal pressure of the cover exceeds an exterior or injection pressure of the hydrogel material. Alternatively, the one way valve arrangement may be a conical nose with a narrower internal opening, again directing the valve structure to a closed state under similar circumstances. The conical configuration facilities insertion of the introducer rod.

The valve structure may comprise a valve body with a longitudinal bore therein, and obturating means associated with the bore. The valve body is configured to be fluidly secured to the edge portion of the prosthetic device. For example, an exterior portion of the valve body may be attached to the edge portion of the cover such that the longitudinal bore is in fluid communication with an interior of the cover. The obturating means is configured to selectively allow passage of filling material, such as hydrogel through the longitudinal bore. The valve body may be generally symmetrical and the longitudinal bore may extend axially within the valve body.

Any suitable filling material may be used, for example polyvinyl alcohol. The filling material may be hydrogel, for example a polyvinyl alcohol material, such as HYPAN®, developed into a fluid or liquid form which will easily pass through the valve structure and subsequently harden. Ideally, the swelling pressure of the resultant hydrogel is in a range similar to, or as close as possible to, a normal lumbar intervertebral disc. Ideally, a hydrogel is used which has similar rheological properties to the normal nucleus.

The prosthesis of the present invention is preferably sized such that an internal surface area of a nuclear cavity is virtually the same as the prosthesis. This will ensure that load distribution within the resulting prosthesis is similar to that of a normal intervertebral disc. The technology of hydrogels at the present time means that the swelling pressure of hydrogel can only approximate to one quarter or one third of a normal disc. So to retain their ability to maintain disc height, it is preferable to form the hydrogel as a solid or semi-solid material, or that the hydrogel harden or cure following injection into the cover.

Alternatively, introduction of a mesh or loose coil or sponge of a fine deformable material into the cover prior to injection of the hydrogel may be carried out. This will have the effect that when the hydrogel sets, the gel, mesh and cover will form an integral structure with similar rheological properties to the normal nucleus. In one alternative embodiment, a fine wire of a radiolucent material is incorporated within the prosthesis to demonstrate the position of a prosthesis in vivo.

In use, one preferred method of insertion of a prosthesis in accordance with the present invention is as follows:

A small skin incision is made with the point of a knife adjacent a damaged intervertebral disc, including an annulus and a nucleus, which has previously been extensively imaged by a Computer Tomography or Magnetic Resonance Imaging. If necessary, confirmation that it is the disc which is painful may be reached by effecting provocative stress discography. This allows percutaneous disc surgery to be carried out by a lateral approach whereby an operating port and trochar is used to insert instruments laterally between adjacent vertebrae in the spine through the paraspinal musculature so entering the disc at the postlateral corner in the safe triangle, inferior to the exiting nerve root. The trochar creates a hole by spreading the fibres of the annulus and provides for access to the nucleus portion of the intervertebral disc.

Chymopapain may be injected into the nucleus to digest the proteoglycan structure thereof. Mechanical action as by a brush with polypropylene bristles may be used to aid the breakdown of any remaining collagen structure to enhance the effect of chymopapain which may then be removed by suction. Subsequently an intervertebral disc nucleus prosthesis in accordance with the present invention is introduced through the disc annulus. The disc annulus comprises an outer ring of strong collagenous fibrous tissue. As previously described, the prosthesis preferably includes a cover having an edge portion shaped to fit within the annulus, and a valve structure. The valve structure, in one preferred embodiment, includes the one-way valve arrangement (or conical nose) and a body that may be knurled or fluted as appropriate. A strengthening portion may be incorporated into the edge portion immediately opposite the valve structure for receiving a distal end of an introducer rod. This allows the relatively atraumatic insertion of the prosthesis cover through the annulus into the space created by the removed nucleus.

Prior to insertion, the external valve structure of the prosthesis is preferably attached to an external introducer tube, and the introducer rod is coaxially positioned within the external introducer tube, and passes through the external valve structure. The introducer rod serves as a temporary stiffening device, allowing a surgeon to apply a pushing force on the cover. Thus, with proper positioning of the introducer rod, engaged with the strengthened portion in the edge portion of the cover, the surgeon can extend the prosthesis cover into the cavity between adjacent vertebrae. The function of the strengthened portion is to protect the cover from damage by introducing the introducer rod. The external introducer may then be rotated to precisely align the strengthened portion of the cover within the annulus. The introducer rod may be movable along its longitudinal axis, or may be releasably attachable to the valve structure by a screw thread. In one preferred embodiment, both the internal and external introducers are attached to a prosthesis prior to insertion, and the prosthesis is folded in such a way as to ensure its ease of passage through the annulus into the nucleus. Such an arrangement may be formed and inserted inside a delivery tube, which would in turn be passed through the operating port to engage the hole in the annulus, and ease passage of the cover into the nuclear cavity.

In a preferred embodiment, the cover preferably contains a collapsible sponge, a mesh, or a fine coil which fills the cover, and has a memory such that after insertion through the annulus into the disc space, the sponge, mesh or coil will return to its previous shape, i.e. the shape of the nucleus, and will expand within the cover to fill the disc space. Once the prosthesis is positioned within the disc space, the introducer rod is withdrawn. Hydrogel material is then introduced into the prosthesis cover via a syringe connected to the external introducer tube. In one preferred embodiment, a distal end of the syringe is directed through the external introducer tube and secured to the valve structure. With this approach, the syringe has an internal seal, to ensure that the hydrogel material passes through the valve structure into the cover, and a locking mechanism to ensure a tight seal with the valve structure. This may be achieved by an arrangement, similar to the tubular spanner, in which the external introducer tube is arranged to receive the syringe, and has grooves to form a bayonet type fitting with pins provided on the syringe.

The syringe of this embodiment further includes a tubular piston rod and a piston that is selectively secured to a screw configured to immediately close the valve structure after injection of the hydrogel. In one embodiment, once a desired volume of hydrogel has been injected into the cover of the prosthesis, and the piston is at the bottom of the syringe, a screw driver may be passed down a center of the piston to insert and tighten the screw to the valve structure.

Alternatively, the screw and the screw driver may be incorporated together into the piston, and the piston rod simply turned to secure the screw to the valve structure.

Alternatively, the external introducer tube may be a cannula including two proximal ports to facilitate injection of the hydrogel material. With this configuration, a syringe is secured to one of the two proximal ports. Hydrogel material is forced from the syringe into the external introducer tube. The external introducer tube, in turn, directs the hydrogel material to the valve structure and then into the prosthetic cover. With the prosthesis filled adequately with hydrogel material to a desired internal pressure, a screw is then passed through the external introducer tube and secured to the valve structure so as to retain the contents of the prosthesis. In the event that the volume of hydrogel material needs to be subsequently altered, this can be performed in a substantially non-traumatic way by merely removing the screw and replacing the contents of the prosthesic cover as necessary.

In an alternative embodiment, where an external valve structure is not used, the introducer rod passes through a conical valve and engages with the strengthened portion of the cover. In this embodiment, the cover can lock with the introducer rod by way of a cruciate flattened section at the distal end of the introducer rod. Once the prosthesis is in position, a cannula is passed over the introducer rod, which is then removed, leaving the cannula in position within the cover. As mentioned hereinbefore, a sponge, mesh or fine wire fill the cover, and may already be present within the cover, or may be inserted through the introducer tube into the cover. Once the cover is expanded in position, hydrogel is injected to fill the cover, encompassing the sponge, or mesh, or coil, before setting within the cover.

One aspect of the present invention will now be described in detail by way of illustration only with reference to the accompanying drawings of FIGS. 1-7.

Figure 1A:
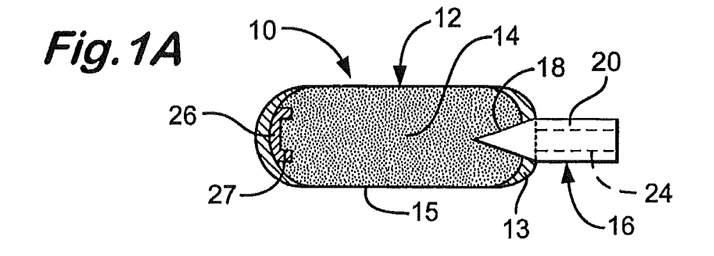
FIG. 1A is a side sectional view of an intervertebral disc nucleus prosthesis in accordance with the present invention.
Figure 1B:
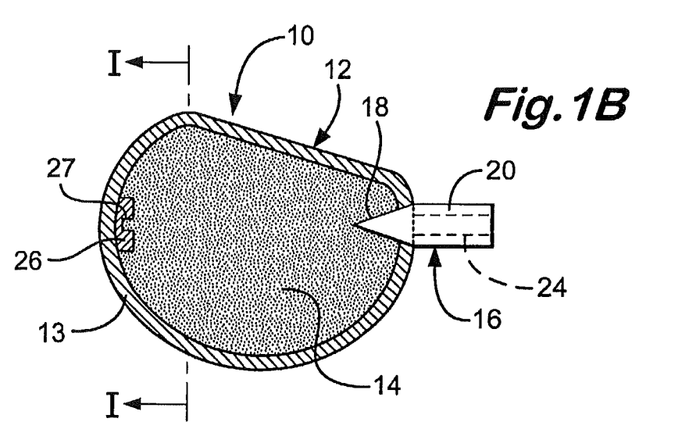
FIG. 1B is a top sectional view of the prosthesis of FIG. 1A.

One embodiment of an intervertebral disc nucleus prosthesis 10 is shown in FIGS. 1A and 1B. The prosthesis 10 includes a cover 12, a filler material 14 and an aperture in the cover comprising a valve structure 16. The cover 12 encompasses the filler material 14 and is sealed to a portion of the valve structure 16. In this regard, the valve structure 16 is fluidly connected to an interior of the cover 12. Notably, the prosthesis 10 is shown FIGS. 1A and 1B in an inflated state.

The cover 12 is generally in the form of a kidney shaped balloon comprising an edge portion in the shape of an annular sleeve 13, having a shape generally similar to that of a car tyre, and two opposed central portions 15 joining each edge of the sleeve 13 to close the cover 12. The sleeve 13 is formed of a resilient deformable material and is shaped to fit within the annulus of an intervertebral disc following removal of the disc nucleus, as described below. The central portions 15 are formed of a flexible thin or weakened material, which allows the passage of the filler material 14 there through under pressure. For example, the flexible material may break or allow the filler material 14 to burst through pores or weakened layers in it under filling pressure. For example, the filler material may be a composite hydroxy apatite paste, configured to harden within the cover 12 between vertebral bodies. When injected under pressure, the filler material will key into holes in the vertebral bodies. The composite hydroxy apatite paste hardens to a cement composition which provides support for the spine, and ingrowth of blood vessels from the vertebral end plates. Eventually the structure will remodel into bone. The cover may alternatively be filled by packing small fragments of a porous hydroxyapetite, such as Apapore, into the cavity, which will absorb blood and bone marrow from the vertebral end plates into its pores. It thus forms a gelatinous semi-solid structure when the blood and bone marrow clots, which will vascularise as previously described and form into bone.

Alternatively, as described in WO 99/02108, the filler material 14 may be a hydrogel material, which is flowable in a first state and relatively rigid in a second state. In one preferred embodiment, the hydrogel material is polyvinyl alcohol based configured to transition from a liquid form in a first state to a hardened or cured form in a second state. For example, the hydrogel material 14 may be HYPAN®, available from Hymedix International, Inc. Preferably, the hydrogel material 14 has a consistency and swelling pressure of a normal disc nucleus. Additionally, as referred to hereinabove, the hydrogel material 14, in an alternative embodiment, may be reinforced by introducing a sponge, mesh or fine wire inside the cover 12, either before introduction of the cover 12 into a disc space, or after via the introducer tube, and injecting the hydrogel material 14 in a liquid state into the cover 12 such that the hydrogel material 14 cures around the mesh. The resulting structure would be more able to resist stresses in a way similar to the normal disc nucleus. The mesh would be introduced into the cover 12 prior to implant, and may be a fine polypropylene thread. With this configuration, the mesh would easily deform to facilitate insertion of the cover 12 into the nucleus, after which the mesh would spring out once again to fill the cover 12.

The valve structure 16 preferably includes a one-way valve 18, and an extension body 20. The one-way valve 18 is integrally formed with the extension body 20, the combination of which forms a longitudinal bore 24 through the valve structure 16. The one-way valve 18 is shown in FIGS. 1A and 1B as being a conical nose. With this configuration, the conical nose restricts flow of the filler material 14 from the cover 12 through the valve structure 16. Alternatively, the one-way valve 18 may be a flap valve (described in greater detail below) to further inhibit back flow of the hydrogel material 14 out from the cover 12.

The filler material 14 may be a soup or growth medium containing nuclear cells or cartilage cells which have been previously removed from the patient, and grown in an artificial medium until enough cells are present to fill the nuclear cavity, These cells may then be injected into the nuclear cavity space so as to substantially fill the cavity with this material, which will allow the body to replicate and rebuild a nuclear structure. In such embodiments, the cover may be made of a degradable plastics material, which, when degraded, will be replaced by a collagen structure which replicates the normal nucleus.

As shown in FIGS. 1A and 1B, the sleeve 13 is secured about the one-way valve 18 portion of the valve structure 16, and the extension body 20 extends from the sleeve 13. The cover includes a shaped strengthened portion 26 positioned opposite the valve structure 16 for providing a seat for the introducer rod. The shaped portion 26 is formed at an interior of the sleeve 13, and may assume a circular form, having a shape such as a slot to engage with a distal end of an introducer rod, as described below. Alternatively, the shaped portion 26 may have a cylindrical recess, into which the distal end of the introducer rod may be rotatably inserted.

Figure 2A:
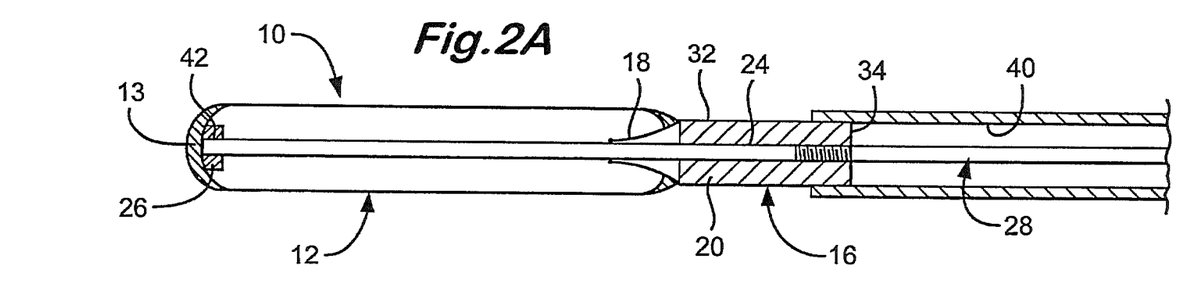
FIG. 2A is an enlarged side sectional view of the prosthesis of FIG. 1A, including an introducer rod and external introducer tube.
Figure 2B:
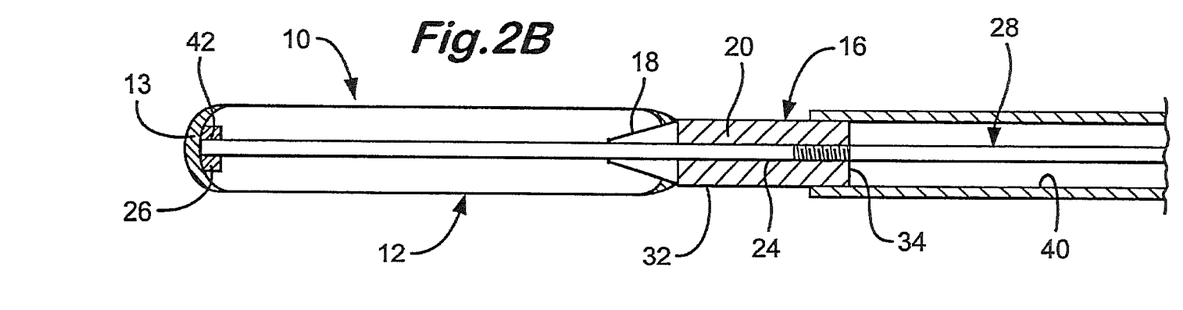
FIG. 2B is an enlarged, top sectional view of the arrangement of FIG. 2A.

The intervertebral disc nucleus prosthesis 10 is shown in greater detail in FIGS. 2A and 2B. Notably, the prosthesis 10 is shown in a deflated state, with the filler material 14 (FIGS. 1A and 1B) removed from the cover 12. Additionally, the prosthesis 10 is shown in FIGS. 2A and 2B as being attached to an introducer rod 28 and an external introducer tube 40. The extension body 20 of the valve structure 16 includes a proximal portion 32 and a distal portion 34. In this regard, the proximal portion 32 is connected to the one-way valve 18.

Use of the introducer rod 28 and the external introducer tube 40 is described in greater detail below. Generally speaking the external introducer tube 40 is an elongate tube having an internal passage. The internal passage of the external introducer tube 40 has a diameter approximating to an outer diameter of the extension body 20. The introducer rod 28 is a relatively stiff member having a diameter less than that of the internal passage of the external introducer tube 40. Thus, the introducer rod 28 is coaxially received in the external introducer tube 40. Further, the introducer rod 28 includes a distal end 42 which is shaped, for example cruciate, slotted, or cylindrical as required, to engage with the shaped portion 26 of the cover. The introducer rod 28 has a diameter approximating to that of the longitudinal bore 24 of the valve structure 16 but has a diameter slightly less than the longitudinal bore so as to be able to freely rotate therein. Alternatively, the introducer rod 28 may be partially screw threaded to engage the inside of the valve structure.

Figure 1C:
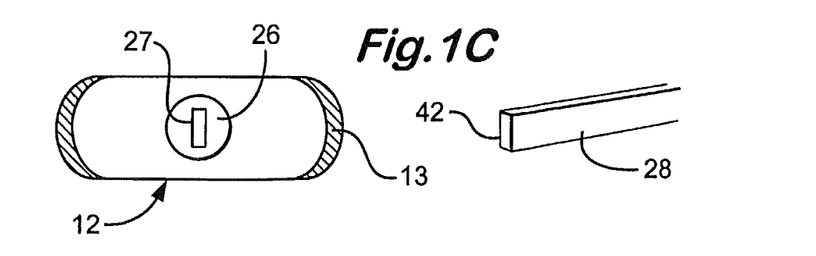
FIGS. 1C and 1D each show a side sectional view of the prosthesis of FIG. 1B taken along the lines I-I, and a perspective view of the distal end of the corresponding introducer rod, used with the external valve structure is not used.
Figure 1D:
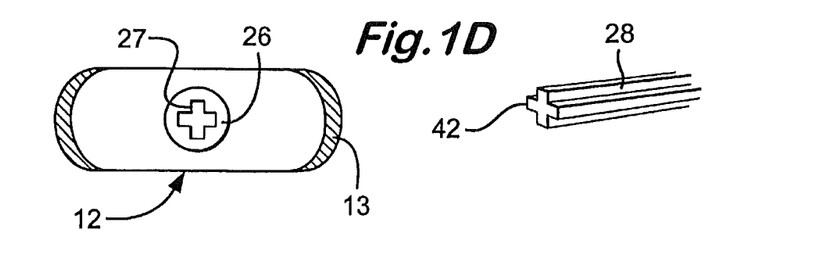

The distal end 42 of the introducer rod 28 may, for example, be flattened and the shaped portion 26 of the cover 12 may have a corresponding elongate slot or groove 27 as shown in FIG. 1C. Alternatively, the distal end 42 may have another shape such as a cruciate form, and the shaped portion 26 may have a corresponding recess or groove 29 as shown in FIG. 1D.

Figure 3A:
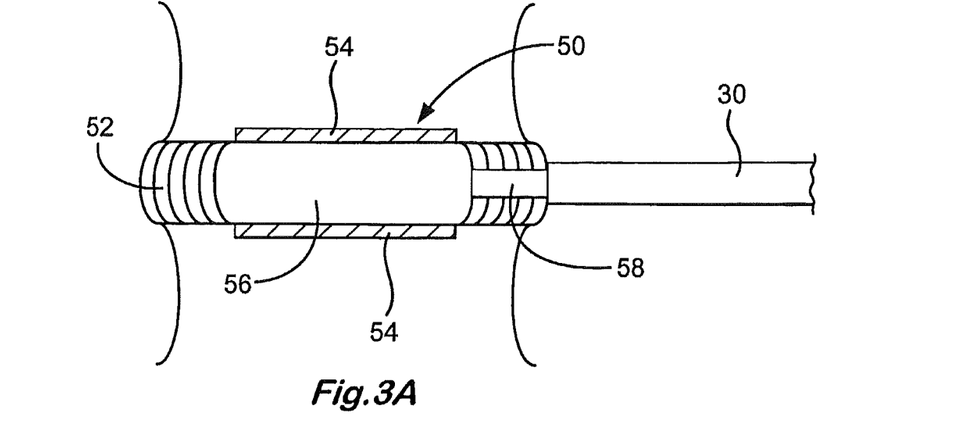
Figure 3B:
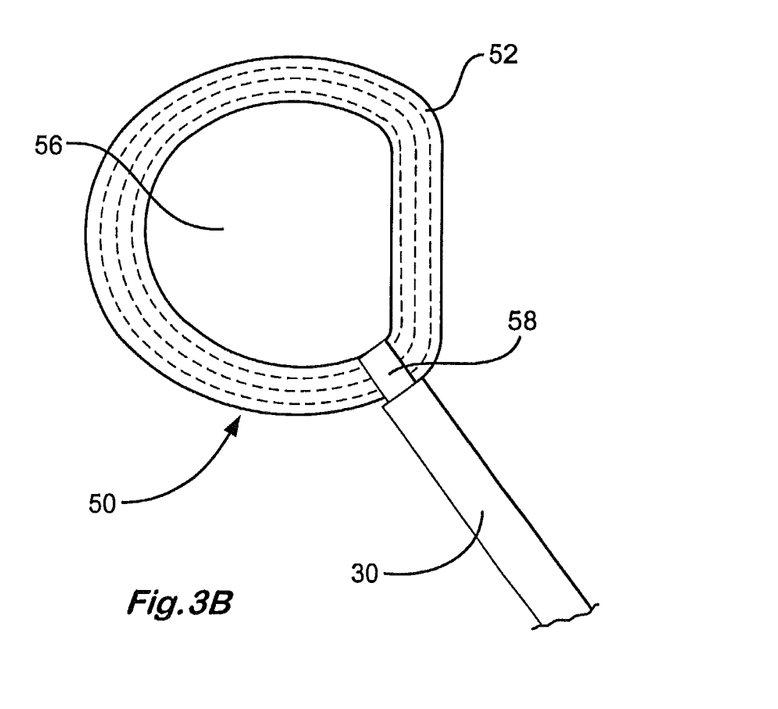
FIG. 3B shows the same view in transverse cross-section.

A preferred method of implanting the intervertebral disc nucleus prosthesis 10 is substantially as follows. A patient is first extensively imaged by traditional means to obtain the level and condition of a damaged disc 50, in the present case a damaged lumbar disc, as shown in FIGS. 3A and 3B. The disc 50 is basically comprised of an annulus 52 and opposing end plates 54 surrounding a nucleus 56.

Following imaging, the nucleus 56 may be removed as is shown in FIGS. 3A and 3B. A preferred lateral percutaneous approach to the disc 50 is used. An incision is made in the skin at the appropriate point, and under imaging control a needle is passed to the posterolateral point of the annulus. The tissues are then dilated by a series of dilating tubes, and finally an operating port 30 is passed down to the level of the annulus. The dilators are then removed, leaving an operating channel. A hole 58 is imparted to access the nucleus 56, and a needle (not shown) of appropriate bore is used to enter the nucleus 56 via the hole 58 and chymopapain is injected to digest the proteoglycan of the nucleus 56. This may be done either prior to the creation of the hole 58 or through it. A polypropylene bristle brush (not shown) may then be inserted to help break down any remaining structure of the nucleus 56 and to aid the digestion of the nucleus 56, which may be removed by suction. Additionally or alternatively, the nucleus may be removed piecemeal by rongeurs.

Subsequently, the external introducer tube 40, otherwise attached to the prosthesis 10 as previously described, is utilized. It should be recalled that at this stage, the cover 12 is deflated or empty. In this position, the longitudinal bore 24 of the valve structure 16 is aligned with the internal passage of the external introducer tube 40. The introducer rod 28 is then coaxially placed through the internal passage and the longitudinal bore 24. The distal end 42 engages the shaped portion 26 of the cover 12, such that the flattened portion fits into the groove 27. Thus, the introducer rod 28 can be extended within the cover 12 to define a preferred diameter of the cover, approximately that of the disc 50 (FIG. 3A), and to hold the cover 12 in the correct orientation.

Figure 4A:
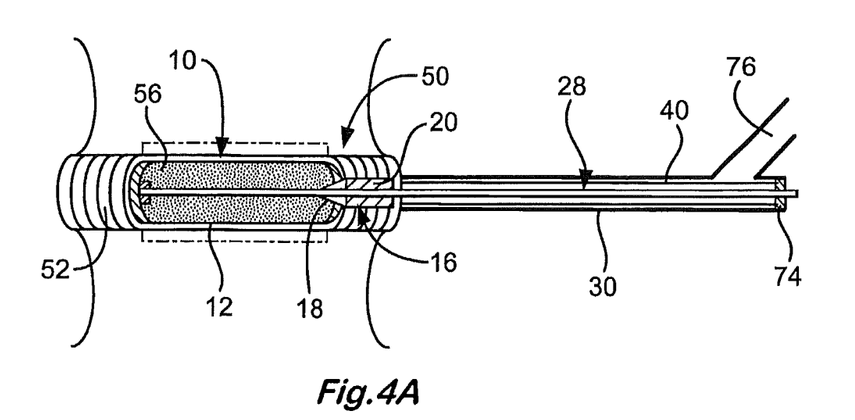
Figure 4B:
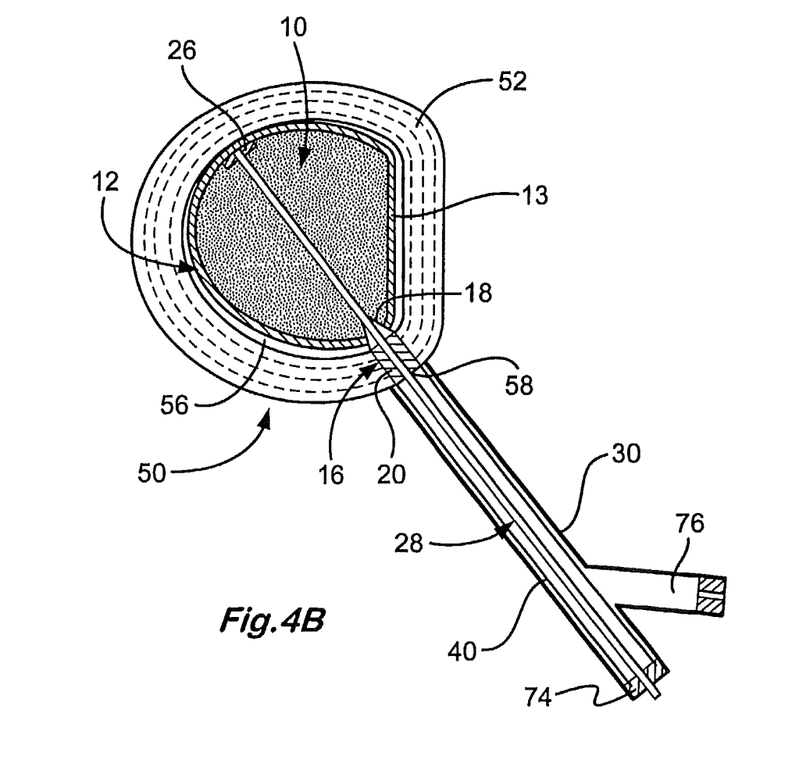
FIG. 4B shows the same view of the cover in accordance with the present invention being introduced in transverse cross-section.

The surgeon then directs the external introducer tube 40 to insert the cover 12 within the disc 50 as shown in FIGS. 4A and 4B. More particularly, the cover 12 is directed through the hole 58 in the annulus 52 to the area once occupied by the nucleus 56. The introducer rod 28 acts as a stiffener, allowing the surgeon to push or force the cover 12 through the annulus 52 and into the area occupied by the nucleus 56. Rotation of the introducer rod 28 causes the sleeve 13 to rotate therewith. Thus the surgeon may control the orientation of the cover to align the sleeve 13 precisely within the disc annulus 52.

Notably, the operating port 30 is shown in FIGS. 4A and 4B as a cannula having two proximal ports 74 and 76. With this configuration, the introducer rod 28 and the external introducer tube 40 are positioned to extend outwardly from the first proximal port 74.

Once the cover 12 has been properly positioned within the space previously occupied by the nucleus 56, the introducer rod 28 is retracted from the external introducer tube 40. More particularly, the introducer rod 28 is withdrawn both from the longitudinal bore 24 of the valve structure 16 and towards the first proximal port 74. The introducer rod 28 may be fully withdrawn from the first proximal port 74 so long as a cap (not shown) is used to prevent any back flow of the hydrogel material 14.

Figure 5A:
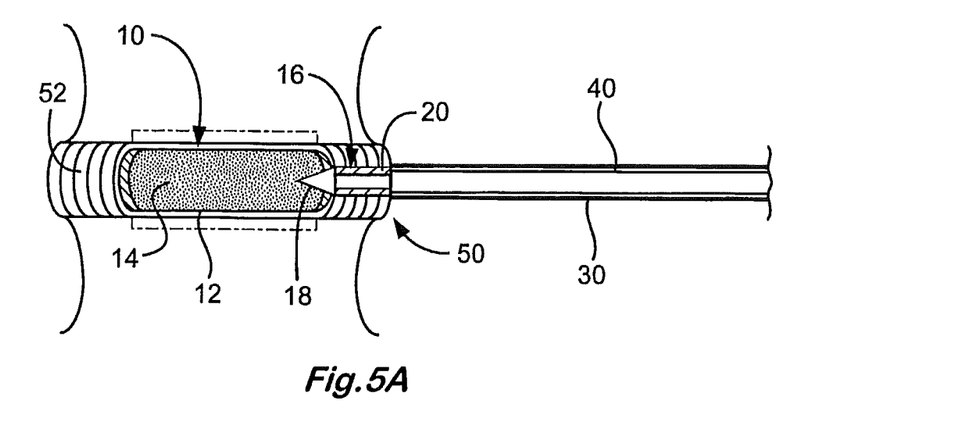
Figure 5B:
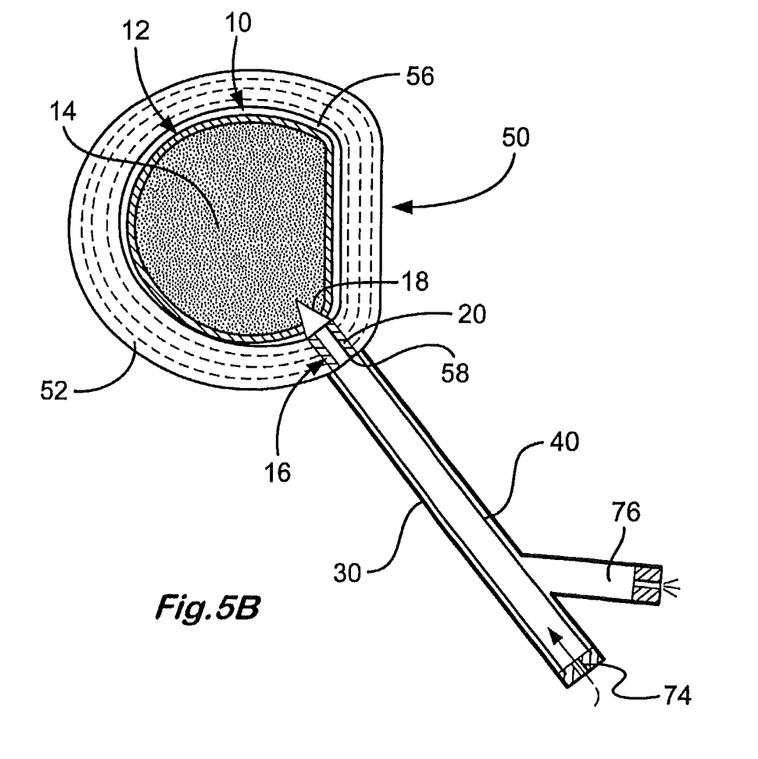
FIG. 5B shows the same view in transverse section.
Figure 5C:
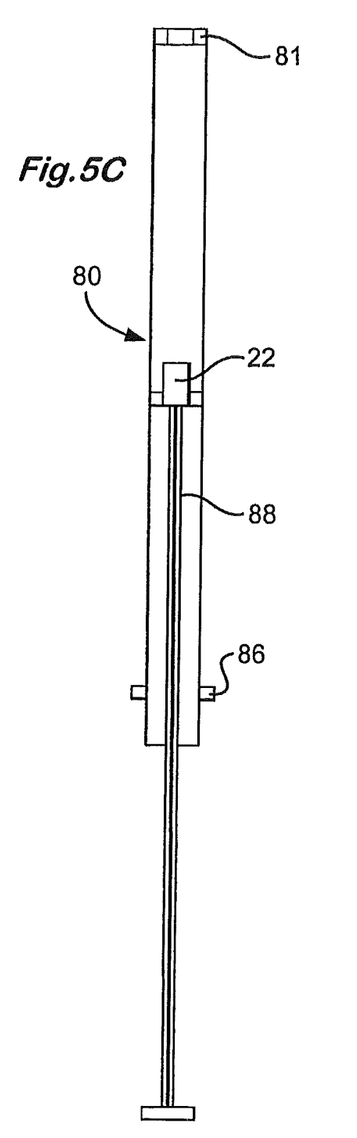
FIGS. 5C and 5D show cross-sectional views of a syringe for use with the prosthesis.
Figure 5D:
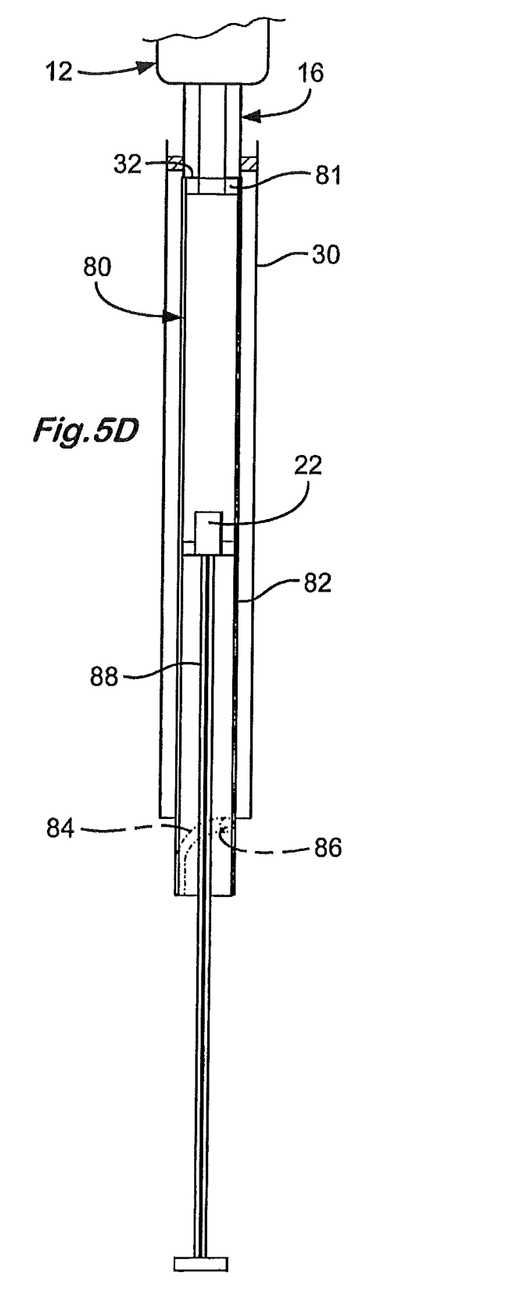

The filler material, which may be a composite ceramic paste, or hydrogel material 14, is then injected into the cover 12, as shown in FIGS. 5A and 5B which depict the prosthetic cover 12 in a fully inflated state. This is achieved in two possible ways. Firstly, a measured amount of the filler material 14 is introduced into a specially designed syringe as shown in FIGS. 5C and 5D. The syringe 80 is long and slender, having a seal 81 at the distal end thereof, and is introduced into the external introducer tube 40 and locks into it in such a way that it forms a seal with the valve structure 16. This may be achieved by a locking mechanism, similar to the tubular spanner arrangement as described previously, wherein the syringe 82 inserted into the introducer tube has two opposed locking grooves 84 for engaging opposed pins 86 provided on the outside of the syringe 80, at the proximal end thereof, in the manner of a bayonet fitting.

The filler material 14 is injected into the prosthesis cover 12 until a piston 88 of the syringe is adjacent the valve structure 16. In a preferred embodiment, the piston of the syringe includes a locking screw 22 embedded in it which can be secured to the proximal portion 32 of the external valve structure. Thus the piston acts as a screw-driver such that after the hydrogel has been injected, the screw engages the hole in the external valve and the screw driver is turned to tighten it. The syringe may then be withdrawn by releasing the pins 86 from the grooves 84.

The filler material 14 may be introduced via the second proximal port 76 and flows down the internal passage 40 of the external introducer tube 40 through the bore 24 in the valve structure 16 and into the deflated prosthetic cover 12 so as to inflate the same to the position shown in FIG. 5A. The introduction of the filler material 14 is continued until the prosthetic cover 12 is adequately filled with the hydrogel material 14.

Figure 6A:
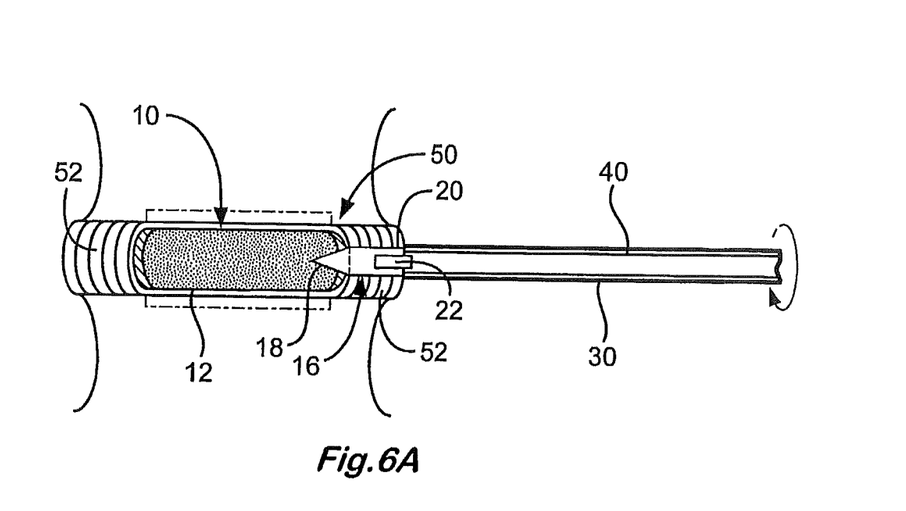
Figure 6B:
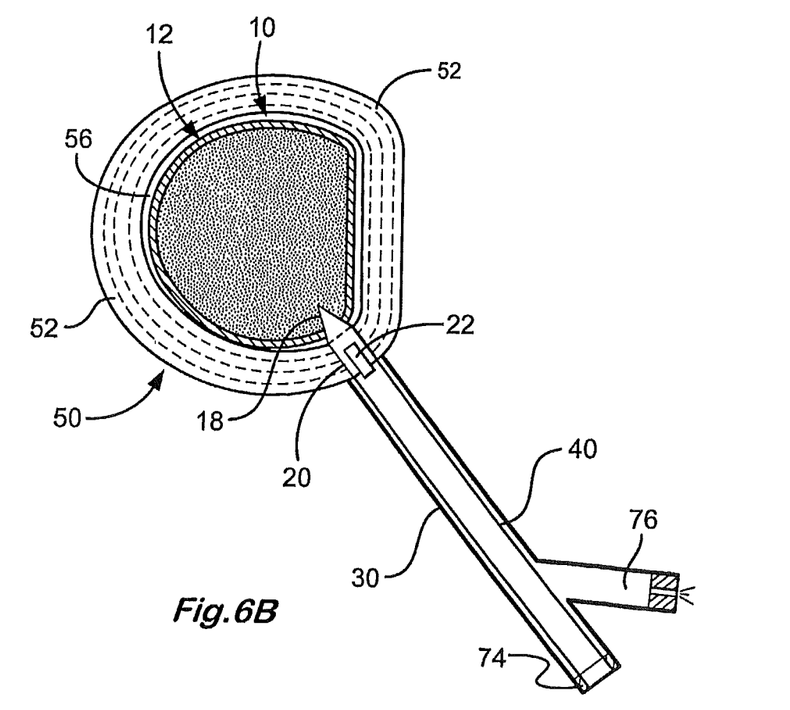
FIG. 6B shows the same view as FIG. 6A in transverse cross-section.

With reference now to FIG. 6, FIGS. 6A and 6B show sealing of the valve structure 16. A screwdriver (not shown) having a set screw 22 is introduced through the external introducer tube 40 and pressed through any remaining filler material 14 until the screw thread on the sealing set screw 22 comes into contact with the internal thread 38 in the extension body 20 of the valve structure 16. The screw 22 is then rotated to close the bore 24. With the screw 22 secured to the valve structure 16, the external introducer tube 40 is disengaged from the prosthesis valve structure 16.

The screw driver can freely rotate with the tubular introducer, and engages with grooves in the valve so preventing rotation of the valve by retaining the tubular screw driver against rotation. The tubular introducer is then disengaged from the valve structure whereupon the screw driver is removed.

In an alternative method of seating the cover, a balloon catheter (not shown) is provided. This is inserted into the cover and inflated to fill the inside and ensure correct positioning. The balloon may then be deflated and an outer filling tube passed over it into the cover. The balloon is then removed and the material injected into the cover. In this case, the external valve structure and introducer rod may not be required, and a simple flap may be provided over the aperture to act as a one-way valve.

By means of the foregoing process, a replacement nucleus pulposis can be inserted between adjacent vertebrae successfully with the removal of pain and incapacity, and prevention of the development of secondary degenerative changes in the disc due to the replacement of damaged or degenerated intervertebral disc. Where the disc has degenerated beyond repair, a percutaneous fusion may be performed by injecting a hydroxy apatite cement into a cover with a strengthened annular sleeve and weakened central portions each joining an edge of the sleeve.

The invention relates therefore to the improved prosthetic device, and to a method for its insertion.

In an alternative form of the prosthesis 10, the valve structure 16 may allow passage of the introducer rod 28 through the flap valve 18 to engage the strengthened portion 26. In this latter case, the introducer rod 28 consists of a cannula with an internal trochar having a shaped internal end which engages the strengthened portion 26. The prosthesis 10 is inserted by pushing it into the nuclear cavity whereupon the trochar is removed. A syringe, containing the hydrogel material or a hydroxy apatite paste 14 is then attached to the external end of the cannula and the hydrogel material or hydroxy apatite paste 14 injected. Since the internal pressure is greater than the injection pressure, the flap valve 18 will close on removal of the cannula. The hole (or operating port) 58 in the annulus 52 will tend to close as the fibres are stretched, so that the prosthesis 10 which by this time is far greater in size than the operating port 58 is easily retained in position.

Figure 7A:
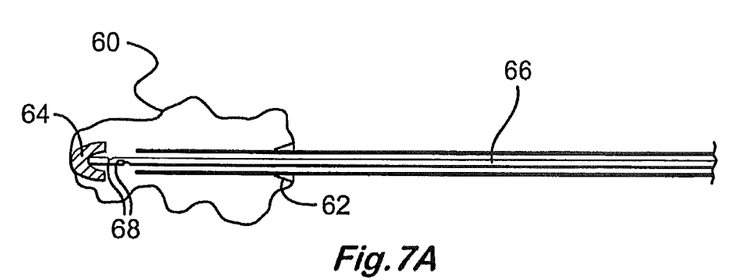
Figure 7B:
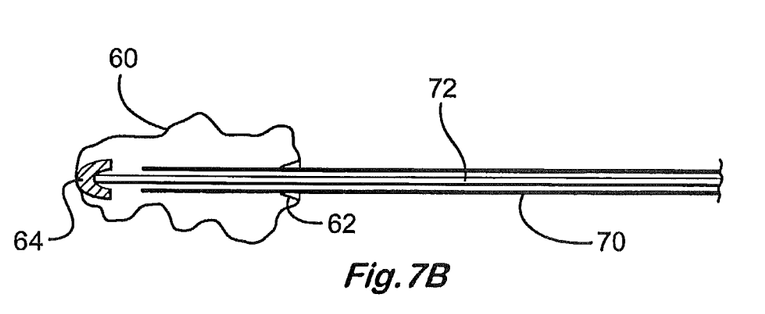

In another embodiment, as shown in FIGS. 7A and 7B, the cover may be a simple flexible jacket 60 having a flap valve 62 as previously described. In this case a radio-opaque marker is provided in the strengthened portion 64 such that its position and orientation may be visualized radiologically. Where no external valve body is provided as in this example, the introducer rod not only introduces the cover into the center of the disc, but also acts as a means by which the filler material is injected into the cover. Therefore, referring to FIG. 7A up to the point where it is shaped at the distal end to engage the strengthened portion, the introducer rod 66 is tubular. Filling material can be injected through the tube into the cover through side openings 68 therein.

Alternatively, referring to FIG. 7B, an outer tube 70 may be inserted over the rod 72 into the aperture of the cover 60. The introducer rod 72 may or may not be removed, and the filling material can be injected through the outer tube 70.

Such a flexible cover preferably includes the mesh structure previously described.

What is claimed is:

1. A prosthetic cover for an intervertebral disc comprising an edge portion being a resiliently deformable annular sleeve shaped to fit within a disc annulus and a pair of opposed flexible central portions each joining the edge portion at an edge of the sleeve, wherein the central portions are formed from a flexible thin material and the edge portion comprises a circumferential ring which is thicker than the central portions, wherein the edge portion includes an aperture for the introduction of a filling material, wherein the annular sleeve is pressurised against the disc annulus on injection of a filling material into the cover, and wherein the central portions are arranged, when the cover is filled with a filling material, to allow the filling material to pass therethrough out of the cover.

2. The prosthetic cover of claim 1 wherein the annular sleeve is generally in the shape of a car tyre.

3. The prosthetic cover of claim 1, wherein in use, the edges of the annular sleeve overlap superior and inferior vertebral end plates.

4. The prosthetic cover of claim 1 wherein the central portions are formed from a material which is absorbable by the body.

5. The prosthetic cover of claim 1 wherein the central portions are adapted to allow the filling material to easily pass therethrough and come into contact with vertebral end plates.

6. The prosthetic cover of claim 1 further comprising a strengthened portion located in the edge portion substantially opposite the aperture, the strengthened portion being shaped to engage and interlock with an elongate introducer member for facilitating orientation of the cover.

7. The prosthetic cover of claim 1 wherein the circumferential ring is curved outwardly with respect to an axial direction between the opposed central portions.

8. The prosthetic cover of claim 1 wherein the annular sleeve comprises an inner surface which is disposed radially outward of the edges of the sleeve which join the central portions with respect to an axial direction between the opposed central portions.

9. The prosthetic cover of claim 1 wherein in use the annular sleeve defines an annular volume of filling material between its inner surface and the edges of the annular sleeve which join the central portions.

10. A prosthetic cover for an intervertebral disc comprising an edge portion being a resiliently deformable annular sleeve shaped to fit within a disc annulus and a pair of opposed flexible central portions each joining an edge of the sleeve, the edge portion including an aperture for the introduction of a filling material, wherein the annular sleeve is pressurised against the disc annulus on injection of a filling material into the cover, and wherein the annular sleeve is curved outwardly with respect to an axial direction between the opposed central portions.

11. The prosthetic cover of claim 10 wherein the annular sleeve is generally in the shape of a car tyre.

12. The prosthetic cover of claim 10, wherein in use, the edges of the annular sleeve overlap superior and inferior vertebral end plates.

13. The prosthetic cover of claim 10 further comprising a strengthened portion located in the edge portion substantially opposite the aperture, the strengthened portion being shaped to engage and interlock with an elongate introducer member for facilitating orientation of the cover.

14. A flexible prosthetic cover shaped to form a replacement nucleus pulposis for an intervertebral disc, the cover comprising an aperture for the introduction of filling material which receives an elongate introducer member therein, and a strengthened portion substantially opposite the aperture shaped to engage and interlock with a distal end of the elongate introducer member, wherein the engagement and interlocking of the strengthened portion with the elongate introducer member prevents relative rotation between the strengthened portion and the elongate introducer member and facilitates rotational orientation of the cover.

15. The flexible prosthetic cover of claim 14 wherein the elongate introducer member is able to be freely rotated in the aperture.

16. The flexible prosthetic cover of claim 14 further comprising an edge portion being a resiliently deformable annular sleeve shaped to fit within a disc annulus, wherein the aperture and the strengthened portion are provided in the edge portion, and the strengthened portion is strengthened with respect to the edge portion.

17. A prosthetic cover for an intervertebral disc comprising an edge portion being a resiliently deformable annular sleeve shaped to fit within a disc annulus and a pair of opposed flexible central portions each joining an edge of the sleeve, the edge portion including an aperture for the introduction of a filling material, wherein the central portions are arranged, when the cover is filled with a filling material, to allow the passage of the filling material therethrough out of the cover.

18. The prosthetic cover of claim 17, wherein in use, the edges of the annular sleeve overlap superior and inferior vertebral end plates.

19. The prosthetic cover of claim 17, wherein the central portions are adapted to allow the filling material to easily pass therethrough and come into contact with vertebral end plates in use.

20. The prosthetic cover of claim 17, wherein the central portions are adapted to allow the passage of filling material therethrough under filling pressure.

21. The prosthetic cover of claim 20, wherein the central portions are formed of a material arranged to break under filling pressure.

22. The prosthetic cover of claim 17, wherein the central portions are formed from a material which is absorbable by the body.

23. A prosthetic cover for an intervertebral disc comprising an edge portion being a resiliently deformable annular sleeve shaped to fit within a disc annulus and a pair of opposed flexible central portions each joining an edge of the sleeve, the edge portion including an aperture for the introduction of a filling material, wherein the annular sleeve is pressurised against the disc annulus on injection of a filling material into the cover, and wherein the annular sleeve comprises an inner surface which is disposed radially outward of the edges of the sleeve which join the central portions with respect to an axial direction between the opposed central portions.

24. The prosthetic cover as claimed in claim 23 wherein the annular sleeve is generally in the shape of a car tyre.

25. The prosthetic cover of claim 23, wherein in use, the edges of the annular sleeve overlap superior and inferior vertebral end plates.

26. The prosthetic cover of claim 23 further comprising a strengthened portion located in the edge portion substantially opposite the aperture, the strengthened portion being shaped to engage and interlock with an elongate introducer member for facilitating orientation of the cover.

27. A prosthetic cover for an intervertebral disc comprising an edge portion being a resiliently deformable annular sleeve shaped to fit within a disc annulus and a pair of opposed flexible central portions each joining an edge of the sleeve, the edge portion including an aperture for the introduction of a filling material, wherein the annular sleeve is pressurised against the disc annulus on injection of a filling material into the cover, and wherein in use the annular sleeve defines an annular volume of filling material between its inner surface and the edges of the annular sleeve which join the central portions.

28. The prosthetic cover of claim 27 wherein the annular sleeve is generally in the shape of a car tyre.

29. The prosthetic cover of claim 27, wherein in use, the edges of the annular sleeve overlap superior and inferior vertebral end plates.

30. The prosthetic cover of claim 27 further comprising a strengthened portion located in the edge portion substantially opposite the aperture, the strengthened portion being shaped to engage and interlock with an elongate introducer member for facilitating orientation of the cover.

* * * * *